(12) United States Patent
Edell et al.

(10) Patent No.: US 6,898,464 B2
(45) Date of Patent: May 24, 2005

(54) OPTICAL TELEMETRY OF DATA AND POWER FOR WIRELESS BIOMEDICAL SENSORS AND ACTUATORS

(75) Inventors: David J. Edell, Lexington, MA (US); Bruce C. Larson, Saratoga, CA (US); Sean V. Sexton, Georgetown, MA (US)

(73) Assignee: Innersea Technology, Bedford, MA (US)

(*) Notice: Subject to any disclaimer, the term of this patent is extended or adjusted under 35 U.S.C. 154(b) by 329 days.

(21) Appl. No.: 09/969,871

(22) Filed: Oct. 3, 2001

(65) Prior Publication Data

US 2002/0107557 A1 Aug. 8, 2002

Related U.S. Application Data (60) Provisional application No. 60/238,219, filed on Oct. 5, 2000.

(51) Int. Cl.[7] ................................................. A61N 1/36
(52) U.S. Cl. .............................. 607/60; 607/32; 128/903
(58) Field of Search .............................. 607/2, 32, 60; 128/903, 904; 600/544

(56) References Cited

U.S. PATENT DOCUMENTS

| | | | |
|---|---|---|---|
| 5,320,098 A | 6/1994 | Davidson | 128/630 |
| 5,387,259 A | 2/1995 | Davidson | 128/630 |
| 5,730,125 A | 3/1998 | Prutchi et al. | 128/637 |
| 5,743,267 A | 4/1998 | Nikolic et al. | 128/673 |
| 5,842,977 A * | 12/1998 | Lesho et al. | 600/300 |
| 6,243,608 B1 | 6/2001 | Pauly et al. | 607/60 |

FOREIGN PATENT DOCUMENTS

WO   WO 01/56653 A1   8/2001   .......... A61N/1/372

* cited by examiner

*Primary Examiner*—Carl H. Layno
(74) *Attorney, Agent, or Firm*—Weingarten, Schurgin, Gagnebin & Lebovici LLP (57) ABSTRACT

An apparatus and corresponding method for providing data communications to and from a location within a body cavity in which an internal transmitter receives a first data stream from an in vivo sensor, electrode, or transducer. The internal transmitter is configured and arranged to asynchronously modulate the first data stream and to provide as an output a first optical signal carrying the asynchronously modulated first data stream. The apparatus further includes an external receiver that is configured and arranged external to the body cavity such that an optical input to the external receiver is optically coupled to the internal transmitter output and receives the optical signal therefrom. The external receiver asynchronously demodulates the received optical signal and provides as an output at least one signal indicative of the first data stream.

25 Claims, 7 Drawing Sheets

OPTICAL TELEMETRY OF DATA AND POWER FOR WIRELESS BIOMEDICAL SENSORS AND ACTUATORS

CROSS REFERENCE TO RELATED APPLICATIONS

This application claims priority under 35 U.S.C. §119(e) to provisional patent application Ser. No. 60/238,219 filed Oct. 5, 2000, the disclosure of which is incorporated by reference herein.

STATEMENT REGARDING FEDERALLY SPONSORED RESEARCH OR DEVELOPMENT

N/A

BACKGROUND OF THE INVENTION

Monitoring of physiological signals for medicine and research presents unique problems that include the acquisition of this information in vivo and the transmission of this information to instruments external to the body where it may be stored and analyzed. These physiological signals may include neural waveforms that result from the firing of individual or groups of neurons, electroencephalogram (EEG) signals from the spatial summation of neural signals, electromyogram (EMG) signals that result from the activation of muscle tissue, and electrocardiogram (EKG) signals that result from contractions of the heart. Other physiological variables that may be monitored, using a suitable sensor, include, for example, temperature, pressure or pH; glucose, $CO_2$ or phosphate concentration; and rate of perfusion. Since many of these physiological signals cannot be determined by non-invasive methods, they must be acquired by the use of implanted sensors, transducers, or electrodes and provided to the external device via transdermal catheters or percutaneous connectors. These catheters and percutaneous connectors typically include physical connections such as wires or cables that relay power, information or both to and from the interior sensors. Catheters and percutaneous connectors, however, are easily damaged, can create a significant potential for infection, and also may be subject to marsupialization by epithelial downgrowth.

Typically, wireless systems used today to provide a wireless communication between the implanted in vivo electronics and sensors and the external device rely on radio frequency (RF) systems. RF systems have several disadvantages, however. For example, for many implant sites RF wireless systems can be too large or heavy. A RF system that is too heavy and too dense compared to the surrounding environment may be subject to non-uniform accelerations compared to the physiological structures surrounding it and physically move, damaging or destroying the physiological structures that were to be monitored. In addition, RF wireless systems are themselves subject to RF interference from telecommunication devices, microwave ovens, computers, cell phones and other common electronic devices.

Within the United States almost 11,000 people each year are victims of a spinal cord injury, of which a significant portion result in at least partial disability of the injured individuals. Half of those injured annually are between the ages of 16 and 30 years old. Currently, there are more than 190,000 people living with some form of paralysis caused by a spinal cord injury. Extensive research is being carried out to help these individuals by monitoring and analyzing neural signals from the regions of the brain associated with muscular control and movement.

Neurons are the fundamental information unit of the nervous system and generate action potentials in order to transfer information from one location to another and to activate muscles for movement. These action potentials consist of roughly three nA ionic currents that flow in the extra cellular spaces between the neurons. These small currents are emitted from localized areas within the neurons, which are on the order of a few microns in size. This current spreads into the volume of the resistive aqueous fluid in the extra cellular space, creating a voltage gradient or electric field therein. The information transfer that occurs in the nervous system can thus be tapped or accessed by implanting electrodes into the extra cellular spaces. These electrodes include small electrically active sites for transducing the small voltages that are created by the neurons and transferring them to instrumentation for analysis outside the body.

Research in the field of neuroprosthetics is hampered by the need for wires to access these bioelectric signals from the nervous system and the percutaneous connectors used to bring these signals out of the body. These extracellular potentials typically have a bandwidth of between 100 Hz to 7 KHz and have a magnitude that is less than 250 $\mu$V and may extend down to the background neural noise floor of approximately 25 $\mu$V.

As discussed above, providing transdermal connections can involve having one or more wires passing through the skin to the implanted electronic device. These wires inadvertently tether, or physically link, the devices to the skull or other fixed structures. As the soft tissues undergo normal physiological motions or volume changes devices implanted within them may move relative to other structures such as the skull connective tissue, or other bones to which the wires are intentionally affixed, or they may attach by the normal healing process. For example, the tethering of the implanted electrodes to the skull by even the finest lead wires may result in non-uniform acceleration of the tethered device due to normal head movement. This non-uniform acceleration of the implanted device can damage neurons due to the movement of the implanted device relative to the brain within the skull. This movement of the implanted device relative to the brain can lead to the damage and destruction of nearby neurons that results in a loss of signal, or a decrease in signal strength, and a loss of information. In addition, the possible long term location drift of the electrodes can result in a lack of stability of the received signals or, as described above, damage or destruction of the adjacent neurons. In addition, the electrode may move entirely out of the potential gradient in the extracellular space, thereby entirely losing the signal of interest.

RF wireless systems that have been implanted require the use of batteries that are far denser than the brain environment. In addition, the volume and mass of the batteries themselves would militate against their use in the neural environment due to compression of the surrounding neurons. RF transmission of power or data also creates substantial electrical interference for implanted devices. In addition, the use of antennas, although small due to the microwave frequencies involved are relatively large and dense relative to the local neural structures and, in addition, could heat local tissue, resulting in further damage.

Practical systems for rehabilitation of an injured spinal cord may require, for example, 1,000–100,000 electrode contacts implanted into regions of the brain associated with the control of movement. To access information from all these electrodes using wire interconnects would result in a wire bundle that would be prohibitively large and stiff, resulting in a large tethering problem. Multiplexing these thousands of signals into even a few wires would not eliminate the tethering problem. In this case the density of wires would still be so great that the differential acceleration caused by normal head motion or acceleration encountered while riding in cars, etc., may cause electrode motion resulting in damage and loss of signals. Also, as normal healing invests the wires with connective tissue, the wires may become attached to other structures resulting in other tethering locations as well.

Therefore it would be advantageous to provide a system for acquiring biomedical information and allowing for transdermal communications that does not involve tethering of the electrodes through wires for either power or signal transmission and that does not require the use of RF systems.

BRIEF DESCRIPTION OF THE INVENTION

The invention is directed to an apparatus and corresponding method for providing data communications to and from a location within a body cavity in which an internal transmitter receives a first data stream from an in vivo sensor, electrode, or transducer. The internal transmitter is configured and arranged to encode the transduced electrical signals forming the first data stream and to asynchronously modulate a first optical signal as an output carrying the encoded first data stream. The apparatus further includes an external receiver that is configured and arranged external to the body cavity such that an optical input to the external receiver is optically coupled to the internal transmitter output and receives the optical signal therefrom. The external receiver asynchronously demodulates the received optical signal and provides as an output at least one signal indicative of the first data stream.

In particular, the internal transmitter includes an encoder module coupled to the first electronic module that receives the data stream therefrom and asynchronously modulates the first data stream to provide, as an output, an optical drive signal modulated with the encoded first data stream. An optical transmitter coupled to the encoder module receives the optical drive signal therefrom and provides the optical signal in response to the optical drive signal. The external receiver includes an optical receiver optically coupled to the output optical signal of the internal transmitter. The optical receiver is configured and arranged to convert the received optical signal into a first electronic signal. A demodulator coupled to the optical receiver receives the first electronic signal from the optical receiver and asynchronously demodulates the first electronic signal and provides at least one output signal representative of the first data stream.

In another embodiment, an internal receiver is provided that is optically coupled to an external transmitter such that bi-directional communications is effected to and from the body cavity.

Other forms, features and aspects of the above-described methods and system are described in the detailed description that follows.

BRIEF DESCRIPTION OF THE SEVERAL VIEWS OF THE DRAWING

The invention will be more fully understood from the following detailed description taken in conjunction with the accompanying drawings in which.

DETAILED DESCRIPTION OF THE INVENTION

Figure 1:
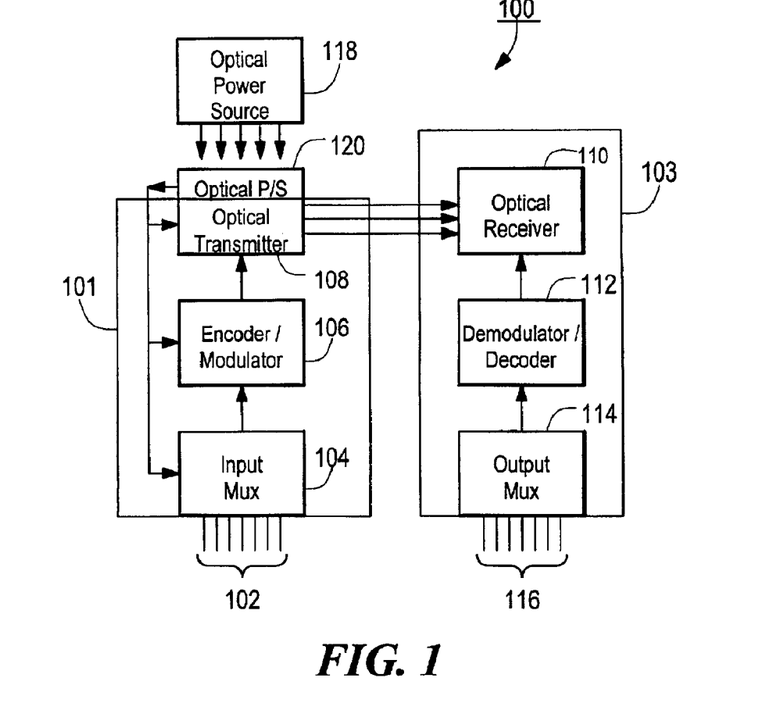
FIG. 1 is a block diagram of an optical telemetry of data and power for wireless biomedical sensors and actuators.
Figure 2:
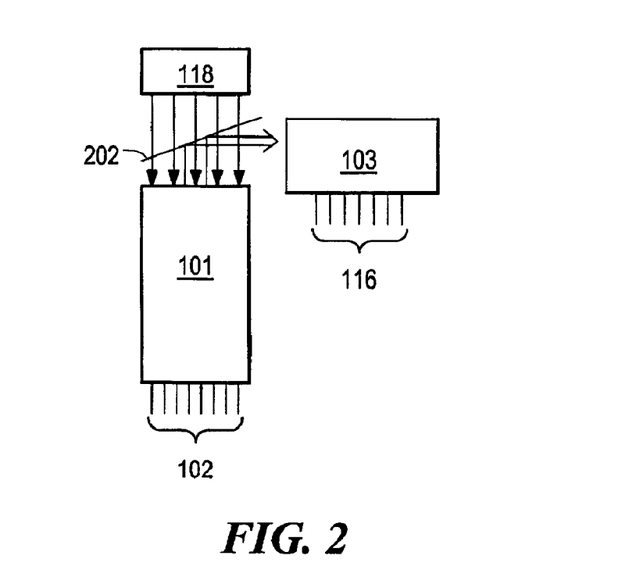
FIG. 2 is a block diagram of another embodiment of the optical telemetry of data and power for wireless biomedical sensors and actuators.
Figure 3:
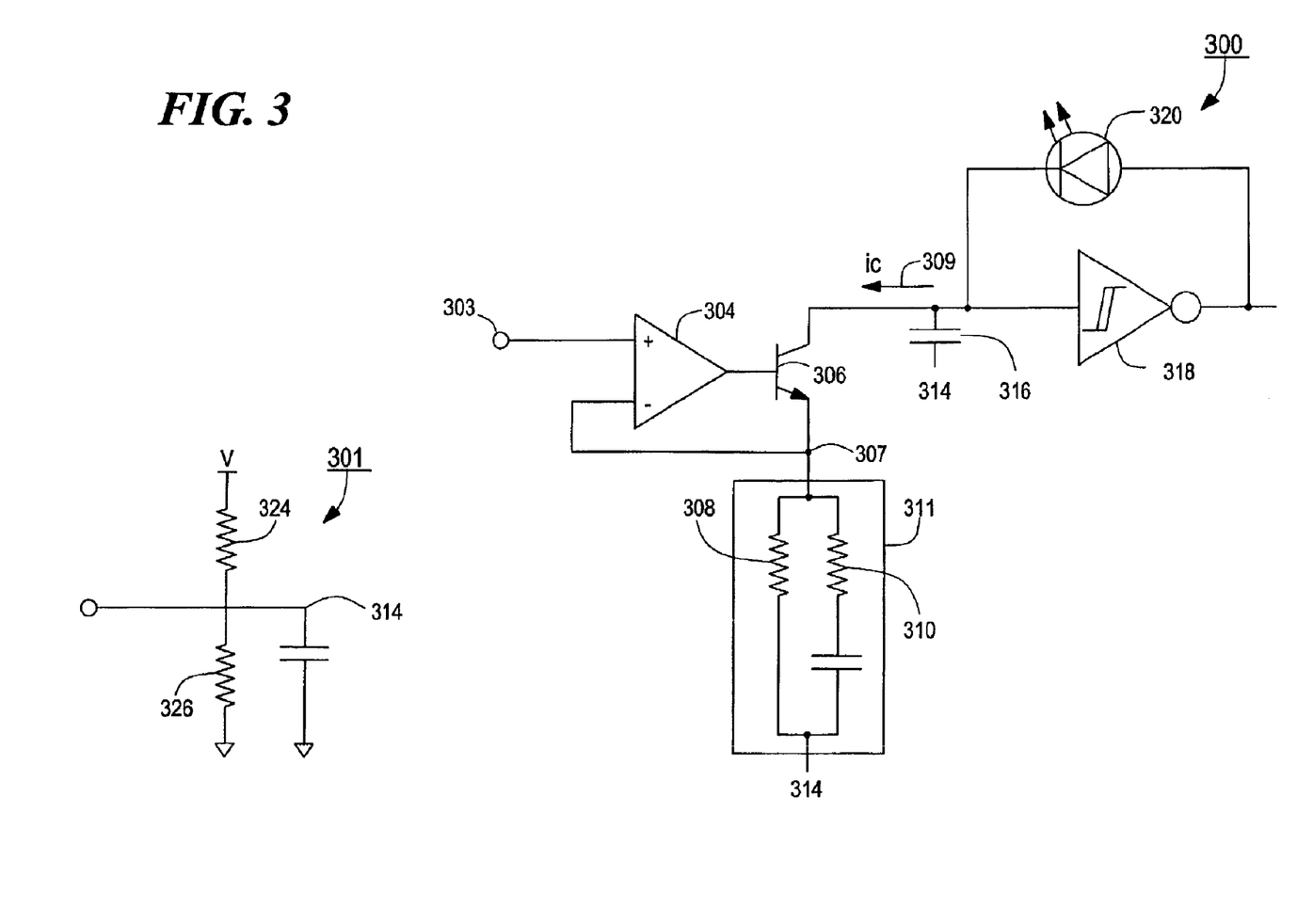
FIG. 3 is a schematic circuit diagram of the modulator block of FIG. 1.
Figure 4:
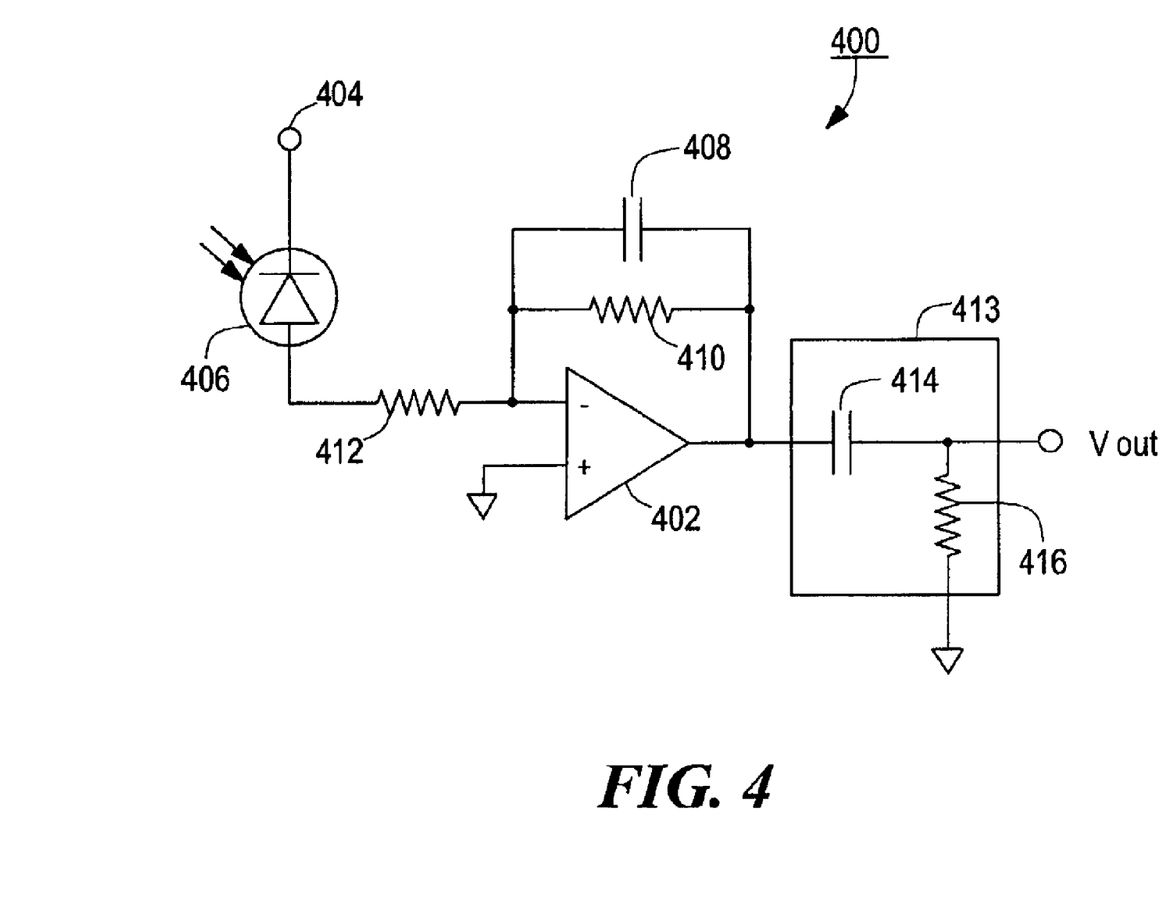
FIG. 4 is a schematic circuit diagram of the optical receiver block of FIG. 1.
Figure 5:
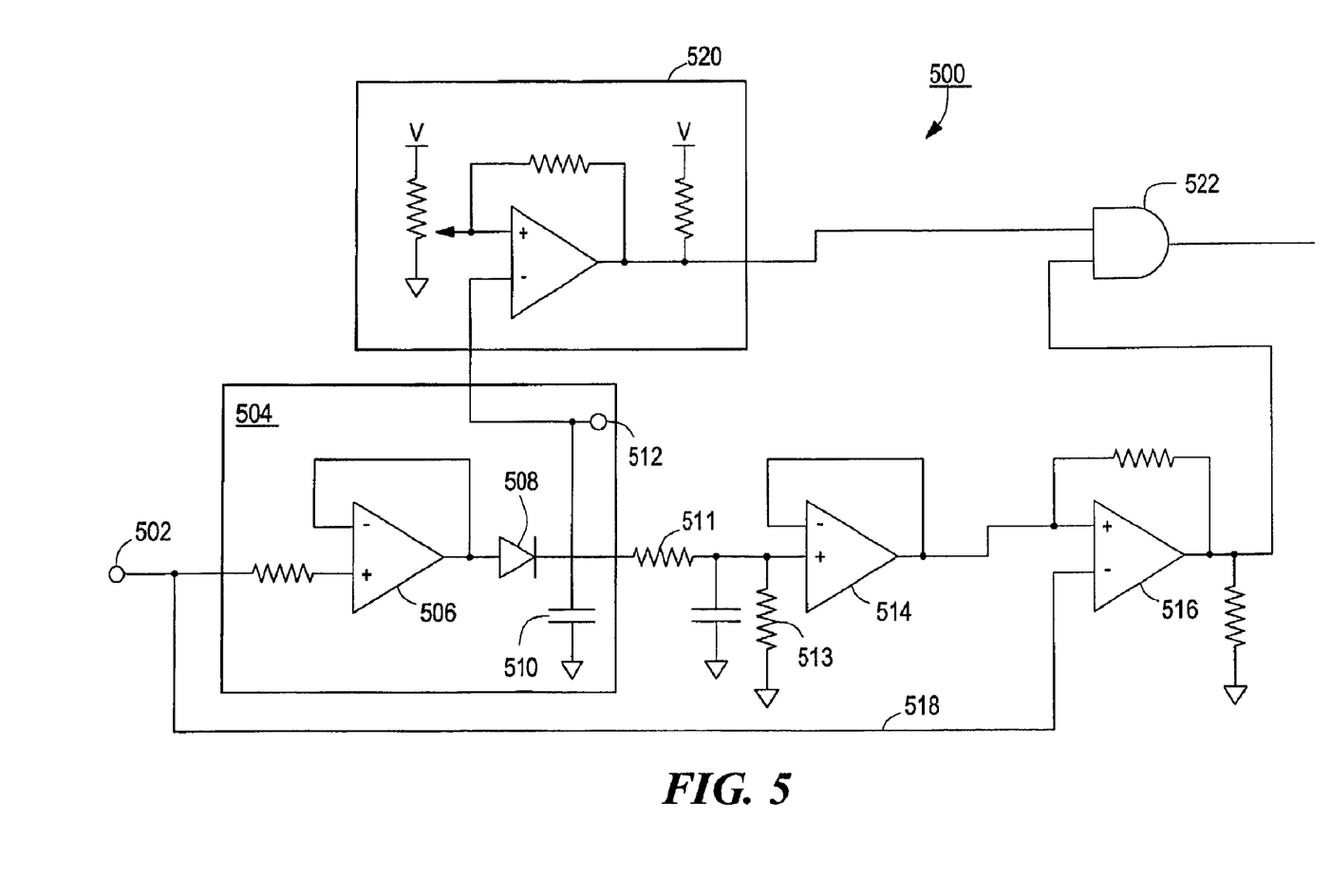
FIG. 5 is a schematic circuit diagram of the demodulator block of FIG. 1.
Figure 6:
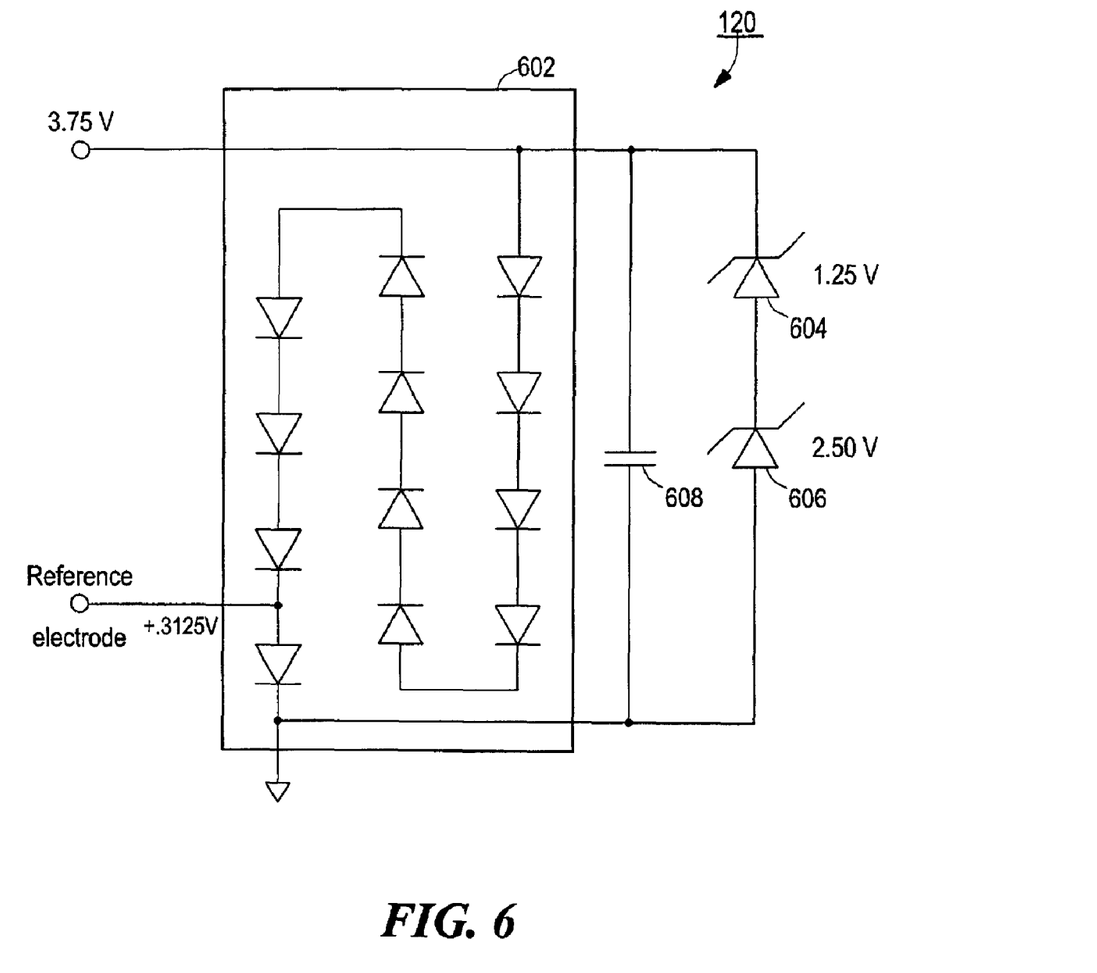
FIG. 6 is a schematic circuit diagram of an optical power supply.
Figure 7:
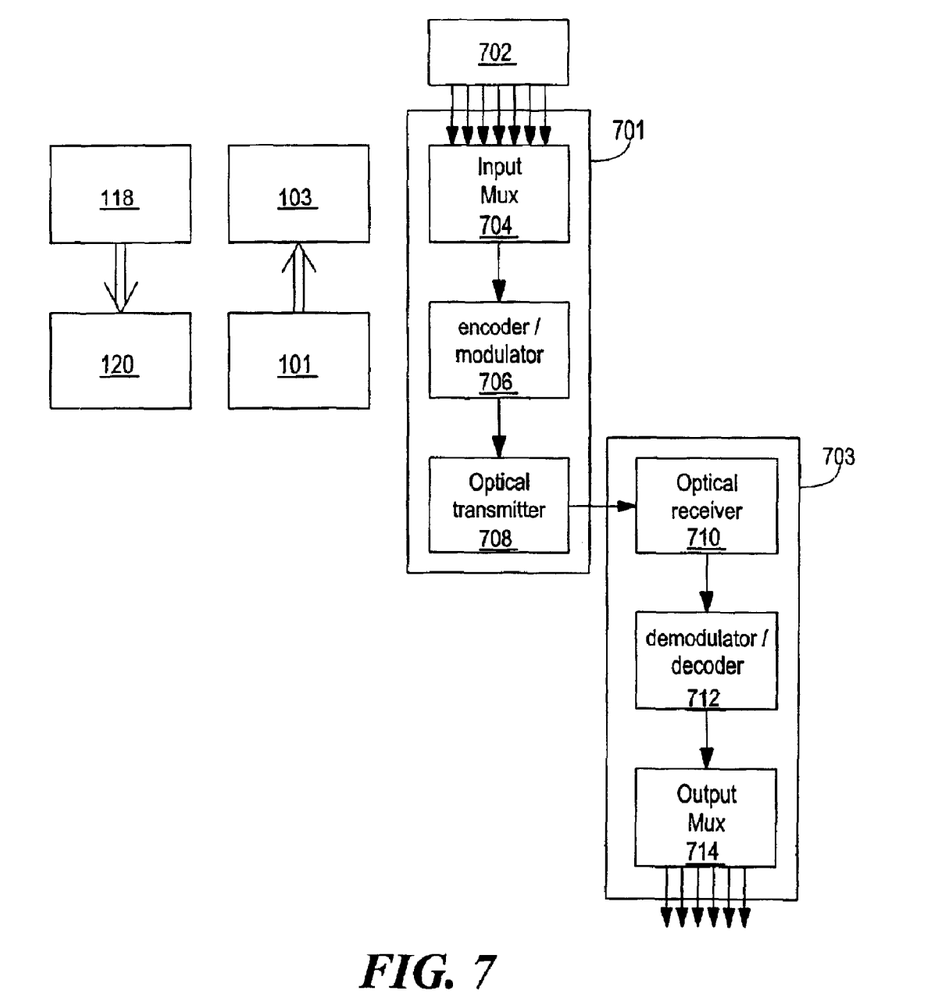
FIG. 7 is a block diagram of an optical telemetry of data and power for wireless biomedical sensors and actuators providing for bi-directional communication.
Figure 8:
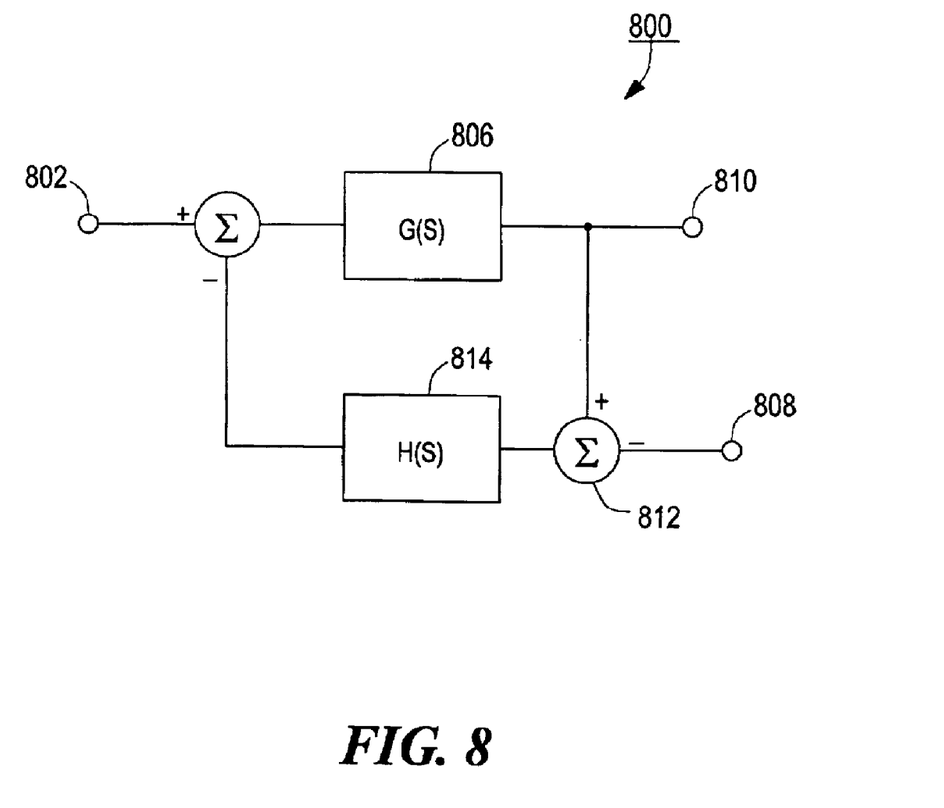
FIG. 8 is a block diagram of an input amplifier and DC/low frequency offset voltage module suitable for use with the present invention.

FIGS. 1 and 2 depict a first embodiment of an apparatus and corresponding method for the optical telemetry of data and power for wireless biomedical sensors and actuators. In particular, FIGS. 1 and 2 depict a unidirectional communications link for providing telemetry data or other operational data from a sensor or other biomedical device implanted within a body cavity. FIGS. 3, 4, and 5 depict particular circuits suitable for performing at least some of the functions illustrated in FIGS. 1 and 2. FIG. 6 is a schematic diagram depicting an optical power supply suitable for providing power to devices implanted in vivo. FIG. 7 depicts another embodiment that provides for bi-directional communications to and from the device or devices implanted within the body cavity, and FIG. 8 depicts a circuit for removing various DC and other low frequency offsets that occur due to the nature of the environment within the body cavity.

As depicted in FIG. 1, an optical telemeter 100 includes one or more electrodes or sensors 102 that are positioned within a body cavity (not shown) and provides, as an output, electrical signals to an internal transmitter 101. As discussed above, signals may include neural waveforms that result from the firing of individual or groups of neurons, electroencephalogram (EEG) signals from the spatial summation of neural signals, electromyogram (EMG) signals that result from the activation of muscle tissue, and electrocardiogram (EKG) signals that result from contractions of the heart. Other physiological variables that may be monitored using a suitable sensor include, for example, temperature, pressure or pH; glucose, $CO_2$ or phosphate concentration; and rate of perfusion.

A multiplexer module 104 within the internal transmitter 101 receives the electrical signals from the electrodes or sensors and combines the electrical signals received from the one or more electrodes into a first data stream, which is provided to encoder/modulator 106. Encoder/modulator 106 encodes the data stream into a first format and uses the encoded data stream to provide a modulated drive signal according to a first modulation scheme. The encoder/modulator 106 provides the modulated drive signal to an optical transmitter 108. Optical transmitter 108 emits an optical signal in response to the optical drive signals, which traverses the skin and is received by an external receiver 103, and in particular by optical receiver 110. Optical receiver 110 converts the received optical signal into an electrical signal that is demodulated and decoded by demodulator/decoder 112 into a second data stream that is demultiplexed by demultiplexer 114. Demultiplexer 114 provides, as an output, one or more output electrical signals that are representative of the corresponding input electrical signals. An optical power source 118 provides light energy that is transmitted through the skin and converted by the optical power supply 120 into electricity that is used to provide power to the internal transmitter 101. The first encoded format can be an analog format or the data stream can be converted into a digital data stream and processed digitally.

There are only a few bands of wavelengths of light that are suitable for transdermal transmission. Thus, the light energy provided by the optical power source 118 may interfere with the optical signal provided by the internal transmitter 101. It is important therefore to provide separate optical paths for the light energy from each module. As shown in FIG. 1, the light energy from the optical power source 118 and the optical signal from the internal transmitter 101 can be oriented such that the optical paths of the two light signals do not intersect; i.e., the two paths are configured and arranged so as not to be on concurrent paths. Alternatively, as depicted in FIG. 2 a dichroic mirror 202 can be inserted into a concurrent optical path that will pass the light energy providing the power to the internal devices, but will reflect onto a new optical path the optical signal carrying the telemetry data to the external receiver 103.

As discussed above, it may not be desirable to provide an internal sensor system with a power source such as a battery due to size, weight, and density limitations. In other circumstances, an internal transmitter as described herein may be coupled to an existing sensor system having an internal battery. In these circumstances, telemetry data needs to be transmitted using the minimum amount of power required to transmit the data at a sufficiently high rate to have a sufficiently high signal to noise ratio for a low data error rate. The less power required by the implanted electronics for a given number of channels, the lower the power requirement of the implant electronics. This allows the optical power supply to use fewer photodiodes and less area to provide the necessary electrical power, resulting in a lighter and smaller optical power supply for a desired signal to noise ratio. In addition, the low amplitudes of some of the signals of interest require low noise front end amplifiers to be used such that the amplifiers need to have the maximum gain for the least amount of electrically generated noise.

In some embodiments the low noise front end amplifiers and other circuits requiring high gain and low noise can be created using MOSFET transistors operating in the sub-threshold or weak inversion operating region where the transconductance to current ratio is maximized. This region of operation provides the maximum signal amplification for a given current and accordingly provides for the highest signal to noise ratio. The weak inversion operating region is determined by the channel width-to-length ratio in the MOSFET and the threshold current. In this way weak inversion or sub-threshold operation is achieved by selecting an appropriate channel width-to-length ratio at a specified current level.

In addition, the use of asynchronous modulation techniques such as amplitude modulation, frequency modulation, and certain pulse modulation schemes that do not require the transmission of extra clock cycles or edges to synchronize the transmitter and receiver require less power. In particular, asynchronous pulse coding techniques do not carry information in the amplitude of the signal. Thus, amplitude variations due to noise or due to movement of the internal transmitter or the external transmitter will not affect the overall error rate of the signal. In one embodiment of the present invention, pulse period encoding is used to encode and modulate the analog biophysical signals. In pulse period modulation, the information is encoded in the time interval between subsequent pulses. Pulse period modulation requires only one pulse per sample and as a result of the variation in the interval between samples, the sampling period rate for a given channel is also variable. Accordingly, the minimum pulse rate must be high enough to meet the Nyquist sampling criteria for the particular signals of interest.

FIG. 3 depicts a pulse period encoder/modulator circuit suitable for use with the presently described optical telemeter. The pulse period encoder/modulator 300 includes an input connection 302 coupled to an op-amp 304. The combination of the op-amp 304 with the bi-polar junction transistor 306 ensures that the voltage present on the input connection 302 is present at the junction 307. This voltage at junction 307 causes collector current, $i_c$ 309, to flow through the integrating capacitor 316. The network 311 allows DC and low frequency components to be shunted to ground via resistor $R_b$ 308, while higher frequency components are passed through the resistor $R_g$ 310 and series capacitor $C_g$ 312. The inverting Schmitt trigger 318 is normally low so that as the collector current $i_c$ 309 flows through integrating capacitor $C_i$ 316, an increasingly negative voltage will be produced. When the negative voltage across the integrating capacitor $C_i$ 316 falls below the low voltage threshold of the inverting Schmitt trigger 318, the output of the inverting Schmitt trigger 318 switches to a high output and provides current through the output light emitting diode (LED) 320. This current will cause the output LED 320 to emit light and, in addition, will charge the integrating capacitor $C_i$ 316 with positive current, raising the voltage across it. When the voltage across the integrating capacitor Ci 316 exceeds the high threshold of the inverting Schmitt trigger 318, the output of the inverting Schmitt trigger 318 will go low, i.e. to a voltage output near the voltage reference potential, and the output LED 320 will cease emitting light. This resetting of the inverting Schmitt trigger 318 to a low output occurs very quickly so that the output LED 320 emits an intense pulse of light for a short period, thus having a low average power value. In the illustrative embodiment, the length of the light pulse is inversely proportional to the amplitude, it would be an obvious modification to provide the inverse functionality, i.e., the length of the light pulse being proportional to the amplitude. The processing at the external receiver would be appropriately modified depending upon the embodiment used. A suitable output LED is a ODR-6610 produced by Opto Diode Corp that has a peak emission wavelength of 660 nm with a 50% spectral bandwidth of 20 nm, and a power efficiency of about 16%. In one embodiment, a platinum reflector can be used as one of the electrical contacts for the LED to provide an increase in the intensity of the output optical signal.

Since the voltage across the integrating capacitor $C_i$ 316 ramps between the hysteresis limits of the Schmitt trigger, the total voltage change across the integrating capacitor $C_i$ 316 will be nearly the same for every cycle. In general, the electrodes and sensors are provided with a differential input signal, where the reference input is at an established voltage reference relative to the body cavity. In particular, the reference electrode is held to float above ground an amount fixed by the ratio of resistors 324 and 326. Thus, the voltage reference node 314 provides the voltage reference potential for all reference points 314 in circuit 301.

FIG. 4 depicts a circuit schematic for an optical receiver that is suitable for use with the presently described optical telemter system. Optical receiver 400 is a transimpedance amplifier in which the optical photo-diode 406 is coupled to a bias voltage 404 and to an operational amplifier 402 configured as a current to voltage converter. The current provided by the photo diode 406 is converted to a voltage by resistor 410 as I*R. Capacitor 408, resistor 412 or both may be added to stabilize the circuit and prevent oscillations. The values of these components are dependent upon the parameters of the operational amplifier used. In addition, output network 413 can be added as a single pole high-pass filter to reduce the low frequency noise and, as described below, any timing errors during demodulation. A suitable photodiode is an VTH2090 silicon PIN photodiode manufactured by EG&G. This photodiode has an active area of approximately 0.85 cm$^2$ and the radiant sensitivity at 660 nm is approximately 0.4 A/W with a capacitance of approximately 70 pF when reverse biased at 30 V with a leakage current of less than 10 nA. The operational amplifier selected was a Burr-Brown OPA655 due to the high speed and low noise of this operational amplifier. It has a 240 MHz gain-bandwidth product, less than 30 fA/√Hz input referred current noise up to 1 MHz, and 6 nV/√Hz input referred above 10 KHz.

Because pulse period modulation is used, the information to be transmitted is contained in the time interval between adjacent pulses. It is important that the threshold level that is selected for starting and stopping the timing between pulses is stable and consistent. A suitable threshold detector circuit is depicted in FIG. 5. In particular, threshold detector 500 includes an input 502 coupled to the photodetector circuit and receiving the output voltage therefrom. Peak detector 504 includes op-amp 506, diode 508 and capacitor 510 and provides a peak output signal at node 512 and a peak output signal to a voltage divider comprised of resistors 511 and 513. The output of the voltage divider circuit is buffered by op-amp 514 and provided as one input to comparator 516. In one embodiment, the voltage divider provides an output voltage across resistor 513 that is ⅕ the peak voltage detected by peak detector 504. The other input to comparator 516 is the input voltage from node 502. Comparator 516 will thus fire and provide a high output to AND gate 522 when the actual input voltage is ⅕ the value of the current peak voltage detected by the peak detector 504. Comparator circuit 520 provides a high output, thus enabling the AND gate 522 to pass the detector pulse from comparator 516, when the peak detected signal is above a predetermined minimum signal level. The output from the comparator 520 is provided to an analog or digital timer (not shown) to determine the time interval between successive pulses As discussed above, different embodiments may encode the data stream in different ways. The processing subsequent to the timing of the interval of subsequent pulses must take the encoding process into account. In the described embodiment, the value of ⅕ the peak value that is used for the comparator circuit 516 is determined by the system parameters to be the part of the optical pulse that has the fastest rise time. As discussed above, the receiver can include a high pass filter on the output to reduce the effect that system noise has on the timing of the interval between adjacent pulses. Since only high frequency components are present and the noise will affect the timing during the fastest rise time portion of the pulse, the noise will have only a small time interval in which to operate and thus will have less affect on the threshold detector.

As discussed above, in some instances it may be advantageous to provide an implanted biomedical device or sensor with an external power source that may be used transdermally. FIG. 6 depicts one embodiment of a circuit schematic of the optical power supply 120. In particular, the optical power supply 120 includes 12 photodiodes 602 connected in a series configuration and a pair of Zener diodes 604 and 606 that are used to regulate the output voltage to 3.75 volts. A filter capacitor 608 is used to provide a low impedance path to ground for high frequency signals to reduce the level of noise on the power supply. In other embodiments in which the desired output voltage is different than the illustrative embodiment, other voltage regulator circuits or combinations of voltage regulator diodes can be used, and in one embodiment no voltage regulation is used at all. The reference electrode can be coupled to the photodiode array 602 such that it is maintained at a predetermined level, which in the illustrative embodiment, is 0.3125 volts. The photo diode array is configured and arranged to receive such that every photodiode receives the maximum amount of light from the optical power source. This generally entails a nearly normal angle of incidence, which also prevents shadowing of one photodiode by another. The optical power source 118 (FIG. 1) can be one or more high power LEDs. In other emboidments, the transdermal optical power supply can be used to recharge implanted rechargeable batteries that have become depleted or can provide a trickle charge to implanted rechargeable batteries to maintain an optimal charge thereon.

FIG. 7 depicts another embodiment in which bi-directional communications are obtained to and from the interior of the body cavity. In particular, FIG. 7 depicts a data and power telemeter system that includes an internal transmitter 101 optically coupled to an external receiver 103 and an optical power source 118 optically coupled to an optical power supply 120, as described above with respect to FIGS. 1, 2 and 6. In order to effect bi-directional communications, a third optical communications path is established between an external transmitter 701 and an internal receiver 703. In particular, a data/command/parameter generator 702 provides one or more outputs of electronic signals. These electronic signals correspond to various commands, data, or parameters that are desired to be communicated with the sensors or other biomedical components that are implanted in vivo within the body cavity. The one or more electronic signals are provided to an external multiplexer 704 that combines the one or more electronic signals into a third data stream. The third data stream is provided to an encoder/modulator module that encodes the third data stream and provides a modulated signal that is suitable for driving an optical transmitter 708. The optical transmitter 708 emits an optical signal in response to the modulated signal received from the encoder/modulator module 706.

The optical signal is received by the optical receiver 710 and converted into an electrical signal. The electrical signal is provided from the optical receiver 710 to the demodulator/decoder 712, that de-modulates the electrical signal received from the optical receiver and decodes the demodulated signal into a fourth data stream. The fourth data stream is provided to a demultiplexer that converts the fourth data stream into one or more electrical signals that correspond to the input electrical signals from the data/command/parameter generator 702.

As discussed above, various types of physiological signals can be sensed and transmitted to an external device that may include a controller. In addition, the data/command/parameter generator 702 can be used to generate signals that can be converted by an implanted device into an ionic current waveform that simulates the firing of an individual or a group of neurons, or that can activate muscle tissue. In this way, the optical bi-directional communications to and from the internal body cavity can be used to sense neural activity that is transmitted to the data/command/parameter generator 702 and used thereby to compute signals to stimulate various physiological functions, such as muscles, when no neural pathway exists without the disadvantages of tethering and physically opening the skin to provide a signal and power pathway.

The problems associated with providing transmission from a location external to the body to a location internal to the body are not as difficult as the converse problem described above. In particular, because power is not at a premium on the transmitter side, the amount of power can be increased, and, concomitantly, the intensity of the optical signal is increased as well. Accordingly, modulation techniques that require synchronization may be used without regard to the amount of power required. Asynchronous modulation techniques such as those described above may also be employed. The circuits described above for use with the internal transmitter and external receiver may be used as well for the internal receiver and the external transmitter described with respect to FIG. 7.

The internal body cavity is a complex environment in terms of the medium in which the sensors, transducers, and electronic devices are implanted. pH and other chemically induced changes in the electrolytes cause slow changes in the electrode-electrolyte interface potentials. These potentials can be orders of magnitude greater than the signals of interest and can interfere with the accurate measurement and transmission of these signals. These time varying potentials and currents can cause offset voltages within the electronic components that will adversely affect the operation and overall accuracy of the data being gathered. These time-varying resistances change fairly slowly over time and hence are a low frequency or DC problem. Accordingly, the removal of these low frequency and DC offsets is an important consideration in an implantable electronic device.

FIG. 8 depicts a block diagram of an input amplifier stage having a low frequency feedback amplifier that is suitable for removing the low frequency and DC offsets in the presently described optical telemeter, or other implantable device. In particular, the input amplifier with offset removal 800 includes an input 802 receiving the data from the sensor, transducer, or other biomedical device. Input 802 is a positive input to difference module 804 that provides a difference output between the positive and negative inputs to forward amplifier 806. Amplifier 806 provides the output signal on line 808 and this output signal is also provided as the positive input to a second difference module 812. The negative input to the second difference module 812 is provided by a reference voltage 808. The reference voltage 808 is a predetermined value and is the determined as being approximately the midrange output voltage of the circuits that follow the input amplifier. The difference output of the second difference module 812 is provided to feedback amplifier 814, the output of which is the negative input to the first difference module 804.

In one embodiment, the forward amplifier and first difference module are a differential amplifier composed of P and N channel MOSFETS, and in which the transfer function can be approximated as:

$$G(s) = \frac{g_{m1}r_{o1}}{sr_{o1}C_{o1} + 1} \quad \text{Eq. 1}$$

where $g_{m1}$ is the transconductance of the amplifier and $r_{o1}$ and $C_{o1}$ are the output resistance and capacitance respectively thereof. Similarly, the transfer function of the feedback amplifier can be approximated as:

$$H(s) = \frac{g_{m2}r_{o2}}{sr_{o1}C_{o2} + 1} \quad \text{Eq. 2}$$

where $g_{m2}$ is the transconductance of the amplifier and $r_{o2}$ and $C_{o2}$ are the output resistance and capacitance respectively thereof. In the illustrated embodiment, the following values for the various amplifiers parameters were given by:

| Amplifier Parameter | Value |
|---|---|
| $g_{m1}$ | 7.5 µA/V |
| $r_{o1}$ | 40 MΩ |
| $C_{o1}$ | 350 fF |
| $g_{m2}$ | .48 µA/V |
| $r_{o2}$ | 625 GΩ |
| $C_{o2}$ | 10 pF |

The output capacitance $C_{o2}$ is much higher than a normal MOSFET output capacitance due to an additional capacitor that has been added across the output of the feedback amplifier. The increased output capacitance is used to provide the necessary pole in the transfer function for the desired frequency response. The very large incremental output resistance $r_{o2}$ would be extremely difficult to fabricate using MOS integrated circuit technology. However, because this circuit is operated in the subthreshold region with very low bias currents, this large resistance is easily obtained. The desired frequency response allows low frequency and DC components to be provided as a feedback signal to be subtracted from the input voltage at the first difference module 804. Accordingly, amplification for DC offset and low frequency voltages is one while higher frequencies are fully amplified prior to encoding and modulating. This prevents saturation of the amplifiers and also maximizes use of the dynamic range of the encoding circuitry.

In some instances, it is desired to implant electrodes within the brain itself to monitor neural signals therein, however, the density of the skull prevents the use of optical signals. In this instance, an aperture can be formed in the skull and a window made of quartz or other suitable material may be used to accommodate the transmission of optical signals therethrough. It is also desirable at times to implant the optical telemeter devices deep in the soft tissues. In a preferred embodiment, a flexible silicone light pipe (a cylinder of an optically clear or translucent silicone) can be used to bring the optical output of the implanted telemeter near the skin for transmission through the skin to external equipment. In a similar fashion, optical power and/or data can be brought to the implanted device using a silicone light pipe. Quartz fibers, or other suitable optically transmissive media can be used as well. If the refractive index of the material used for the light pipe is sufficiently different from that of tissue, high efficiency transmission will occur. Or, if the refractive index is close to tissue, it may be necessary to coat the light pipe with a suitable reflective material or with a material with a different refractive index. As discussed above, it is important, particularly when monitoring neural signals in the brain, to ensure that any motion of the head does not cause movement of the neural monitoring implant and subsequent damage to the surrounding neurons. Packaging the implantable devices in a density neutral manner such that the density of the packaging is equal to the density of the surrounding internal cavity environment would help to ensure that the implantable device accelerates and decelerates at substantially the same rate as the physiological structures that surround it. In particular, density matching can be achieved with the use of a low density overcoat encapsulating the implantable devices. Any low density overcoat can be used to encapsulate the implantable device such as epoxy or urethene. In a preferred embodiment, a low density silicone overcoat is used to encapsulate the implantable devices. The final density of the assembly of the overcoat encapsulation and implantable devices can be adjusted by adding hollow glass micro-spheres to the silicone or by foaming the silicone until the density of the encapsulated assembly equals that of the surrounding environment.

Those of ordinary skill in the art should further appreciate that variations to and modification of the above-described methods, apparatus and system for providing optical telemetry and communications to and from an implantable device within a body cavity may be made without departing from the inventive concepts disclosed herein. Accordingly, the invention should be viewed as limited solely by the scope/ spirit of the appended claims.

What is claimed is:

1. An apparatus for providing data communications to and from a location within a body cavity, the apparatus comprising:
   an internal transmitter receiving a first data stream, the internal transmitter configured and arranged to asynchronously modulate the first data stream using an asynchronous modulation scheme and to provide as output a first optical signal carrying the asynchronously modulated first data stream; and
   an external receiver configured and arranged external to the body cavity, the external receiver having an optical input optically coupled to the internal transmitter output, wherein the optical input of the external receiver receives the optical signal from the internal transmitter, the external receiver further configured and arranged to asynchronously demodulate the optical signal and to provide as an output at least one signal indicative of the first data stream.

2. The apparatus of claim 1
   wherein the internal transmitter includes: an encoder module coupled to a first electronic module and receiving the data stream therefrom, the encoder configured and arranged to asynchronously modulate the first data stream using said asynchronous modulation scheme and to provide as an output an optical drive signal modulated with the encoded first data stream; and an optical transmitter coupled to the encoder module and receiving the optical drive signal therefrom, the optical transmitter configured and arranged to provide the optical signal according to the optical drive signal; and
   wherein the external receiver includes: an optical receiver optically coupled to the output optical signal of the internal transmitter, the optical receiver configured and arranged to convert the received optical signal into a first electronic signal; and a demodulator coupled to the optical receiver and receiving the first electronic signal therefrom, the demodulator configured and arranged to asynchronously demodulate the first electronic signal and to provide at least one output signal representative of the first data stream.

3. An apparatus for providing data communications to and from a location within a body cavity, the apparatus comprising:
   a internal transmitter receiving a first data stream, the internal transmitter configured and arranged to asynchronously modulate the first data stream using an asynchronous modulation scheme and to provide as output a first optical signal carrying the asynchronously modulated first data stream; and
   an external receiver configured and arranged external to the body cavity, the external receiver having an optical input optically coupled to the internal transmitter output, wherein the optical input of the external receiver receives the optical signal from the internal transmitter, the external receiver further configured and arranged to asynchronously demodulate the optical signal and to provide as an output at least one signal indicative of the first data stream,
   wherein the asynchronous modulation scheme is a pulse position modulation scheme.

4. The apparatus of claim 3 wherein the pulse position modulation scheme is a pulse period modulation scheme.

5. An apparatus for providing data communications to and from a location within a body cavity, the apparatus comprising:
   a internal transmitter receiving a first data stream, the internal transmitter configured and arranged to asynchronously modulate the first data stream using an asynchronous modulation scheme and to provide as output a first optical signal carrying the asynchronously modulated first data stream; and
   an external receiver configured and arranged external to the body cavity, the external receiver having an optical input optically coupled to the internal transmitter output, wherein the optical input of the external receiver receives the optical signal from the internal transmitter, the external receiver further configured and arranged to asynchronously demodulate the optical signal and to provide as an output at least one signal indicative of the first data stream,
   wherein the asynchronous modulation scheme is an amplitude modulation scheme.

6. The apparatus of claim 1 wherein the asynchronous modulation scheme is a frequency modulation scheme.

7. An apparatus for providing data communications to and from a location within a body cavity, the apparatus comprising:
   a internal transmitter receiving a first data stream, the internal transmitter configured and arranged to asynchronously modulate the first data stream using an asynchronous modulation scheme and to provide as output a first optical signal carrying the asynchronously modulated first data stream;
   an external receiver configured and arranged external to the body cavity, the external receiver having an optical input optically coupled to the internal transmitter output, wherein the optical input of the external receiver receives the optical signal from the internal transmitter, the external receiver further configured and arranged to asynchronously demodulate the optical signal and to provide as an output at least one signal indicative of the first data stream;
   wherein the internal transmitter includes an encoder module coupled to a first electronic module and receiving the data stream therefrom, the encoder configured and arranged to asynchronously modulate the first data stream using said asynchronous modulation scheme and to provide as an output an optical drive signal modulated with the encoded first data stream, and an optical transmitter coupled to the encoder module and receiving the optical drive signal therefrom, the optical transmitter configured and arranged to provide the optical signal according to the optical drive signal;
   wherein the external receiver includes an optical receiver optically coupled to the output optical signal of the internal transmitter, the optical receiver configured and arranged to convert the received optical signal into a first electronic signal, and a demodulator coupled to the optical receiver and receiving the first electronic signal therefrom, the demodulator configured and arranged to asynchronously demodulate the first electronic signal and to provide at least one output signal representative of the first data stream; and further including:

an internal input multiplexer having a plurality of inputs each coupled to one of a first plurality of data streams, the input multiplexer further including an output coupled to the encoder, the input multiplexer configured and arranged to multiplex the plurality of data streams into an output signal of a first multiplexed data stream, the output of the input multiplexer coupled to the encoder for encoding thereby and wherein the first optical signal is modulated with the encoded first multiplexed data stream, wherein the first optical signal is transmitted and received by the optical receiver, the demodulator providing as an output a second multiplexed data stream and further including an output multiplexer having an input coupled to the demodulator and receiving the second multiplexed data stream, the output multiplexer having a plurality of outputs, the output multiplexer configured and arranged to de-multiplex the plurality of data streams into a plurality of output signals, wherein each of the plurality of output signals corresponds to at least one of the plurality of data streams.

8. An apparatus for providing data communications to and from a location within a body cavity, the apparatus comprising:

a internal transmitter receiving a first data stream, the internal transmitter configured and arranged to asynchronously modulate the first data stream using an asynchronous modulation scheme and to provide as output a first optical signal carrying the asynchronously modulated first data stream;

an external receiver configured and arranged external to the body cavity, the external receiver having an optical input optically coupled to the internal transmitter output, wherein the optical input of the external receiver receives the optical signal from the internal transmitter, the external receiver further configured and arranged to asynchronously demodulate the optical signal and to provide as an output at least one signal indicative of the first data stream;

an external transmitter disposed external to the body cavity, the external transmitter receiving a second data stream, the external transmitter configured and arranged to modulate the second data stream using a modulation scheme and to provide as an output a second optical signal carrying the modulated second data stream; and an internal receiver configured and arranged internal to the body cavity such that an input to the internal receiver is optically coupled to the external transmitter output and receives the second optical signal therefrom, the internal receiver further configured and arranged to demodulate the second optical signal and to provide as an output at least one signal representative of the second data stream, wherein bi-directional communications are obtained to and from the body cavity.

9. The apparatus of claim 8 wherein the modulation scheme is a asynchronous modulation scheme.

10. The apparatus of claim 9 wherein the modulation scheme is a pulse modulation scheme.

11. The apparatus of claim 8 wherein the modulation scheme is an asynchronous modulation scheme.

12. The apparatus of claim 11 wherein the modulation schema is a pulse position modulation scheme.

13. The apparatus of claim 12 wherein the pulse position modulation scheme is a pulse period modulation scheme.

14. An apparatus for providing data communications to and from a location within a body cavity, the apparatus comprising:

a internal transmitter receiving a first data stream, the internal transmitter configured and arranged to asynchronously modulate the first data stream using an asynchronous modulation scheme and to provide as output a first optical signal carrying the asynchronously modulated first data stream;

an external receiver configured and arranged external to the body cavity, the external receiver having an optical input optically coupled to the internal transmitter output, wherein the optical input of the external receiver receives the optical signal from the internal transmitter, the external receiver further configured and arranged to asynchronously demodulate the optical signal and to provide as an output at least one signal indicative of the first data stream;

an external transmitter disposed external to the body cavity, the external transmitter receiving a second data stream, the external transmitter configured and arranged to modulate the second data stream using a modulation scheme and to provide as an output a second optical signal carrying the modulated second data stream; and an internal receiver configured and arranged internal to the body cavity such that an input to the internal receiver is optically coupled to the external transmitter output and receives the second optical signal therefrom, the internal receiver further configured and arranged to demodulate the second optical signal and to provide as an output at least one signal representative of the second data stream, wherein bi-directional communications are obtained to and from the body cavity, wherein a second electronic module includes a plurality of outputs and provides a second plurality of data streams therefrom, and further includes an external input multiplexer having a plurality of inputs each coupled to a corresponding one of the plurality of outputs of the second electronic module, the external input multiplexer further including an output coupled to the external encoder, the input multiplexer configured and arranged to multiplex the second plurality of data streams into an external output signal of a third multiplexed data stream, the output of the external input multiplexer coupled to the external encoder for encoding thereby and wherein the second optical signal is modulated with the encoded second multiplexed data stream, and wherein the second optical signal is transmitted and received by the internal optical receiver, the internal demodulator providing as an output a fourth multiplexed data stream and further including an internal output multiplexer having an input coupled to the internal demodulator and receiving the second multiplexed data stream therefrom, the internal output multiplexer having plurality of outputs, the internal output multiplexer configured and arranged to de-multiplex the fourth multiplexed data stream into a second plurality of output signals, wherein each of the second plurality of output signals corresponds to at least one of the second plurality of data streams.

15. An apparatus for providing data communications to and from a location within a body cavity, the apparatus comprising:

a internal transmitter receiving a first data stream, the internal transmitter configured and arranged to asynchronously modulate the first data stream using an asynchronous modulation scheme and to provide as output a first optical signal carrying the asynchronously modulated first data stream;

an external receiver configured and arranged external to the body cavity, the external receiver having an optical input optically coupled to the internal transmitter output, wherein the optical input of the external receiver receives the optical signal from the internal transmitter, the external receiver further configured and arranged to asynchronously demodulate the optical signal and to provide as an output at least one signal indicative of the first data stream; and a light pipe optically coupled to the optical transmitter and configured and arranged to transfer the first optical signal from the internal transmitter to a first transmit location.

16. The apparatus of claim 15 wherein the light pipe is a silicone light pipe.

17. The apparatus of claim 16 wherein the silicone light pipe is an optical fiber.

18. An apparatus for providing data communications to and from a location within a body cavity, the apparatus comprising:

a internal transmitter receiving a first data stream, the internal transmitter configured and arranged to asynchronously modulate the first data stream using an asynchronous modulation scheme and to provide as output a first optical signal carrying the asynchronously modulated first data stream; and an external receiver configured and arranged external to the body cavity, the external receiver having an optical input optically coupled to the internal transmitter output, wherein the optical input of the external receiver receives the optical signal from the internal transmitter, the external receiver further configured and arranged to asynchronously demodulate the optical signal and to provide as an output at least one signal indicative of the first data stream, wherein the internal transmitter includes at least one circuit using MOSFET transistors operating in the subthreshold region of operation.

19. An apparatus for providing data communications to and from a location within a body cavity, the apparatus comprising:

a internal transmitter receiving a first data stream, the internal transmitter configured and arranged to asynchronously modulate the first data stream and to provide as output a first optical signal carrying the asynchronously modulated first data stream; and at least one overcoat layer encapsulating the internal transmitter, at least one overcoat layer providing the encapsulated internal transmitter with a density substantially matching the density of the body cavity.

20. The apparatus of claim 19 wherein at least one overcoat layer includes a low density foam material and wherein the density of the low density foam material is adjusted to substantially match the body cavity surrounding the internal transmitter using hollow glass micro-spheres.

21. The apparatus of claim 20 wherein the low density foam material is a low density silicone foam.

22. An offset cancellation stage for reducing low frequency and DC offset voltages in an electronic device including an input amplifier having a first input implanted within a body cavity, providing a first data stream as telemetry from a location within a body cavity, the first data stream provided by a first electronic module, the offset cancellation stage comprising:

a feedback circuit having the first input of the input amplifier coupled to one input of a first difference module, the output of the difference module provided to the input amplifier having a first transfer function, the input amplifier providing as an output signal, a second difference module having as a first input the output signal and as a second input a reference signal coupled thereto, the second difference module providing the difference between the output signal and the reference signal as an input to a feedback module having a second transfer function, the feedback module providing a feedback signal to the second input of the first difference module wherein the output of the first difference module is the difference between the first data stream and the feedback signal, wherein the second transfer function is selected to remove low frequency and DC offset components from the first data stream.

23. A method for providing data communications to and from a location within a body cavity, the method comprising the steps of:

providing at least one internal electrical signal;

encoding at least one internal electrical signal;

modulating an internal optical transmitter to provide an optical signal in an asynchronous modulation scheme according to the encoded at least one internal electrical signal;

transmitting the modulated optical signal through the body cavity;

receiving the modulated optical signal externally to the body cavity by an external optical receiver;

demodulating the received optical signal to provide an external demodulated electrical signal; and decoding the external demodulated electrical signal to provide an external electrical signal representative of the internal electrical signal.

24. The method of claim 23, the method further comprising the steps of:

providing at least one external electrical signal;

encoding at least one external electrical signal;

modulating an external optical transmitter to provide an optical signal in a modulation scheme according to the encoded at least one external electrical signal;

transmitting the modulated optical signal into the body cavity;

receiving the modulated optical signal internally within the body cavity by an internal optical receiver;

demodulating the received optical signal to provide an internal demodulated electrical signal; and decoding the external demodulated electrical signal to provide an internal electrical signal representative of the external electrical signal.

25. The method of claim 23 further wherein the step of transmitting the modulated optical signal through the body cavity includes the steps of:

transmitting the modulated optical signal;

receiving the modulated optical signal at an input of a light transmissive light pipe;

transmitting the modulated optical signal through the light pipe to a first transmitting location; and transmitting from an output of the light pipe the modulated optical signal through the body cavity from the first transmitting location.

* * * * *

UNITED STATES PATENT AND TRADEMARK OFFICE
CERTIFICATE OF CORRECTION

PATENT NO. : 6,898,464 B2
APPLICATION NO. : 09/969871
DATED : May 24, 2005
INVENTOR(S) : David J. Edell et al.

It is certified that error appears in the above-identified patent and that said Letters Patent is hereby corrected as shown below:

Column 14, Claim 12, line 2, "schema" should read --scheme--.

Signed and Sealed this

Eighth Day of August, 2006

JON W. DUDAS
*Director of the United States Patent and Trademark Office*